(12) United States Patent
Hayama et al.

(10) Patent No.: US 12,190,510 B2
(45) Date of Patent: Jan. 7, 2025

(54) ULTRASONIC IMAGE PROCESSING DEVICE, ULTRASONIC IMAGE PROCESSING METHOD, AND PROGRAM

(71) Applicant: National Center for Global Health and Medicine, Tokyo (JP)

(72) Inventors: Hiromasa Hayama, Tokyo (JP); Yukio Hiroi, Tokyo (JP)

(73) Assignee: NATIONAL CENTER FOR GLOBAL HEALTH AND MEDICINE, Tokyo (JP)

( * ) Notice: Subject to any disclaimer, the term of this patent is extended or adjusted under 35 U.S.C. 154(b) by 341 days.

(21) Appl. No.: 17/777,613

(22) PCT Filed: Nov. 20, 2020

(86) PCT No.: PCT/JP2020/043400
§ 371 (c)(1),
(2) Date: May 17, 2022

(87) PCT Pub. No.: WO2021/100856
PCT Pub. Date: May 27, 2021

(65) Prior Publication Data
US 2023/0342919 A1    Oct. 26, 2023

(30) Foreign Application Priority Data
Nov. 22, 2019   (JP) .................................. 2019-211735

(51) Int. Cl.
*G06K 9/00*     (2022.01)
*G06T 7/00*     (2017.01)

(52) U.S. Cl.
CPC .. *G06T 7/0012* (2013.01); *G06T 2207/10132* (2013.01); *G06T 2207/30048* (2013.01)

(58) Field of Classification Search
None
See application file for complete search history.

(56) References Cited

U.S. PATENT DOCUMENTS

2019/0099153 A1    4/2019   Weinberg

FOREIGN PATENT DOCUMENTS

| JP | 2002224063 A | 8/2002 |
|---|---|---|
| JP | 2003135468 A | 5/2003 |
| WO | 2013057999 A1 | 4/2013 |

OTHER PUBLICATIONS

Hayama, H. et al., "About new evaluation method of afterload in pulmonary hypertension", Abstracts of the 5th Study Group for hemodynamics of right ventricular and adult congenital heart diseases, 2019.

(Continued)

*Primary Examiner* — S J Park
(74) *Attorney, Agent, or Firm* — Kowert, Hood, Munyon, Rankin & Goetzel, P.C.; Gareth M. Sampson (57) ABSTRACT

Disclosed herein is an ultrasonic image processing device including: a first image acquiring unit configured to acquire a first ultrasonic Doppler image; a second image acquiring unit configured to acquire a second ultrasonic Doppler image; and an arithmetic operation unit configured to derive a reflected wave component of a pulse pressure wave on the basis of the first ultrasonic Doppler image and the second ultrasonic Doppler image.

7 Claims, 9 Drawing Sheets

(56) References Cited

OTHER PUBLICATIONS

Lopez-Candales, A. et al., "Differences in the duration of total ejection between right and left ventricles in chronic pulmonary hypertension", Echocardiography, May 5, 2011, vol. 28, No. 5, pp. 509-515.
Johnson, L. et al., "Clinical Characteristics of 53 dogs with doppler-derived evidence of pulmonary Hypertension", 1992-1996, J. Vet. Intern. Med., 1999, vol. 13, No. 5, pp. 440-447.
Hiromasa, Hayama, et al., "Review on Novel Evaluation for Pulmonary Hypertension Using Doppler Echocardiography", NCGM, 2019, 30 pgs.
Hiromasa, Hayama, et al., "Review on Novel Evaluation for Pulmonary Hypertension Using Doppler Echocardiography", 154th Regular Meeting of Medical Society of Toho University (Abstract), 2019, 2 pgs.
Hiromasa, Hayama, et al., 5th Study Group for Hemodynamics of Right Ventricular and Adult Congenital Heard Diseases (HERVAC), 2019, 21 pgs.
International Search Report, PCT Application No. PCT/JP2020/043400, mailed Jan. 19, 2021, 6 pgs.
Written Opinion, PCT Application No. PCT/JP2020/043400, date of completion Jan. 4, 2021, 3 pgs.
Office Action in JP Application No. 2021-558471, date mailed May 14, 2024, with translation, 9 pgs.
J. Feng, A. W. Khir, Journal of Biomechanics, "Determination of wave speed and wave separation in the arteries using diameter and velocity", 43 (2010), pp. 455-462.

| Variables | Baseline model (EF+EDV+E/e') | | Baseline model +PASP | | Baseline model +Pb | |
|---|---|---|---|---|---|---|
| | HR | P | HR | P | HR | P |
| EF | 0.982 | 0.004 | 0.083 | 0.008 | 0.984 | 0.013 |
| E/e' | 1.029 | 0.001 | 1.023 | 0.014 | 1.017 | 0.088 |
| PASP | | | 1.017 | 0.019 | | |
| Pb | | | | | 1.066 | 0.003 |

ULTRASONIC IMAGE PROCESSING DEVICE, ULTRASONIC IMAGE PROCESSING METHOD, AND PROGRAM

PRIORITY CLAIM

This application is a 371 national stage filing of INTERNATIONAL APPLICATION NO.: PCT/JP2020/043400, which claims priority to Japanese Patent Application No. 2019-211735, filed Nov. 22, 2019, the content of which is incorporated herein by reference.

TECHNICAL FIELD

Embodiments disclosed herein relate to an ultrasonic image processing device, an ultrasonic image processing method, and a program.

BACKGROUND ART

Conventionally, as a technology for non-invasively measuring a forward wave component and a reflected wave component of a hemodynamic index, an ultrasonic diagnostic device disclosed in the following Patent Literature 1 is known. This ultrasonic diagnostic device measures a blood flow velocity of a measurement portion on the basis of an ultrasonic reception signal, measures a local blood pressure of the measurement portion on the basis of the ultrasonic reception signal and an output of a hemodynamometer, calculates a pulse wave velocity on the basis of a time derivative of the blood flow velocity and a time derivative of the local blood pressure, and performs an operation of separating hemodynamics such as a wave intensity (WI) and the like into a forward component and a reflected component using the pulse wave velocity.

In addition, as this kind of technology, an ultrasonic imaging device disclosed in the following Patent Literature 2 is known. In ultrasonic imaging, this ultrasonic imaging device measures a value having physical compliance with a blood flow velocity near a biotissue, recognizes shape data of the biotissue using an echo signal reflected from an inspection target to which ultrasonic waves are emitted, detects a blood flow velocity near the tissue from the echo signal, extracts speed information (target speed information) desired by a detector, sets a target blood flow model, and determines a speed of an actually measured speed distribution value that is in compliance with a speed distribution estimated from the model.

SUMMARY

A pulse wave transmitted through an artery includes waves transmitted from a heart side to a peripheral side as a forward wave component and waves transmitted from the peripheral side to the heart side as a reflected wave component. For example, in a diagnosis of pulmonary hypertension, a pressure value of a reflected wave component (hereinafter referred to as "reflected wave pressure") in a pulmonary artery is an important index. Determination of a diagnosis, a classification, a degree of severity, and an effect of treatment of pulmonary hypertension is performed using a catheter (combo-wire) that is able to simultaneously measure a pressure and a flow velocity for obtaining a reflected wave pressure of a pulmonary artery. However, since a technique for obtaining a reflected wave pressure of a pulmonary artery using a catheter has high invasiveness, there is a large burden on a patient, and measurement cannot be performed simply and repeatedly.

The ultrasonic diagnostic devices disclosed in Patent Literatures 1 and 2 described above can measure a blood flow velocity of a pulmonary artery using ultrasonic waves. However, for the ultrasonic diagnostic device disclosed in Patent Literature 1, it is difficult to obtain a blood pressure value of a pulmonary artery with high accuracy, and thus, as a result, it is difficult to obtain a reflected wave pressure in a pulmonary artery with high accuracy.

Disclosed embodiments are in view of the problems described above, and an advantage thereof is to provide an ultrasonic image processing device, an ultrasonic image processing method, and a program capable of obtaining a pressure of a reflective wave in blood non-invasively and with high accuracy.

According to some embodiments, there is provided an ultrasonic image processing device including: a first image acquiring unit configured to acquire a first ultrasonic Doppler image; a second image acquiring unit configured to acquire a second ultrasonic Doppler image; and an arithmetic operation unit configured to derive a reflected wave component of a pulse pressure wave on the basis of the first ultrasonic Doppler image and the second ultrasonic Doppler image.

According some embodiments, in the ultrasonic image processing device described above, the first ultrasonic Doppler image may be an image based on a blood flow in a tricuspid valve, and the second ultrasonic Doppler image may be an image based on a blood flow in a right ventricular outflow tract.

According some embodiments, in the ultrasonic image processing device described above, the arithmetic operation unit may: calculate a pressure value on the basis of the first ultrasonic Doppler image; calculate a flow velocity value and a pulse wave speed value on the basis of the second ultrasonic Doppler image; and calculate a forward wave component and a reflected wave component of the pulse pressure wave on the basis of at least the calculated pressure value, the calculated flow velocity value, the calculated pulse wave speed value, and a blood density.

According some embodiments, in the ultrasonic image processing device described above, the arithmetic operation unit may calculate a forward wave component (P+) and a reflected wave component (P−) of the pulse pressure wave by performing arithmetic operations represented in the following Equation 1, Equation 2, and Equation 3 using the pressure value (P) based on the first ultrasonic wave Doppler image, the flow velocity value (U) and the pulse wave speed value (c) based on the second ultrasonic Doppler image, and the blood density (ρ).

$$dU+ = (dP + \rho c dU)/2\rho c \qquad \text{(Equation 1)}$$

$$dU- = -(dP - \rho c dU)/2\rho c \qquad \text{(Equation 2)}$$

$$P\pm = \Sigma dP\pm \qquad \text{(Equation 3)}$$

According some embodiments, in the ultrasonic image processing device described above, the arithmetic operation unit may output a value acquired by adding the reflected wave component of the pulse pressure wave to a heart function index as a processing result.

According some embodiments, in the ultrasonic image processing device described above, the arithmetic operation unit may output information based on a trend of the reflected wave component of the pulse pressure wave on a time axis as a processing result.

According to some embodiments, in the ultrasonic image processing device described above, the arithmetic operation unit may output a period of a time at which the reflected wave component of the pulse pressure wave becomes a peak value on the time axis and a time at which the reflected wave component of the pulse pressure wave becomes a value that is half the peak value as a processing result.

According to some embodiments, there is provided an ultrasonic image processing method including: a step of acquiring a first ultrasonic Doppler image; a step of acquiring a second ultrasonic Doppler image; and a step of deriving a reflected wave component of a pulse pressure wave on the basis of the first ultrasonic Doppler image and the second ultrasonic Doppler image.

According to some embodiments, there is provided a program causing a computer of a diagnosis device to execute processing of: acquiring a first ultrasonic Doppler image; acquiring a second ultrasonic Doppler image; and deriving a reflected wave component of a pulse pressure wave on the basis of the first ultrasonic Doppler image and the second ultrasonic Doppler image.

According to some embodiments, a pressure of a reflective wave in blood can be obtained non-invasively and with high accuracy.

DETAILED DESCRIPTION OF EMBODIMENTS

Here, an ultrasonic image processing device, an ultrasonic image processing method, and a program according to the disclosed embodiments will be described with reference to the drawings.

Figure 1:
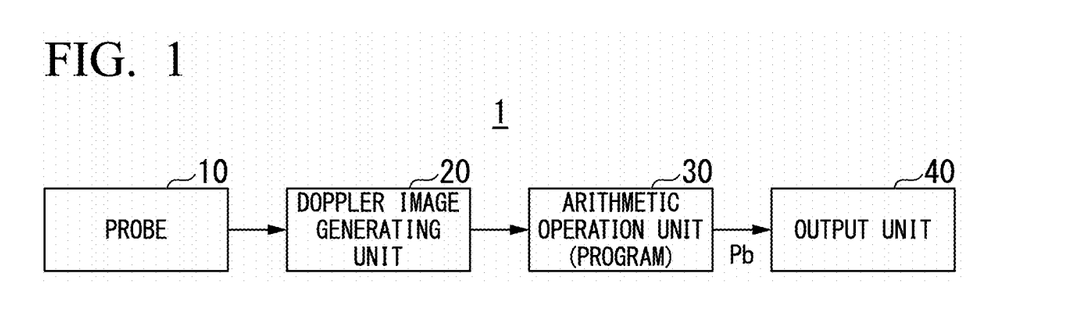
FIG. 1 is a block diagram illustrating an example of an ultrasonic image processing device according to an embodiment of the disclosed embodiments.

FIG. 1 is a block diagram illustrating an example of an ultrasonic image processing device 1 according to an embodiment. For example, the ultrasonic image processing device 1 includes a probe 10, a Doppler image generating unit 20, an arithmetic operation unit 30, and an output unit 40.

The probe 10 includes an output part that outputs ultrasonic waves and an input part that receives reflected ultrasonic waves as an input. The probe 10 outputs an ultrasonic signal representing input ultrasonic waves to the Doppler image generating unit 20. In addition, the ultrasonic image processing device 1 may acquire a tricuspid valve counterflow waveform by continuous wave Doppler or may acquire a right ventricular outflow tract waveform by pulsed Doppler.

The Doppler image generating unit 20 generates an ultrasonic Doppler image on the basis of an ultrasonic wave signal input from the probe 10. For example, the Doppler image generating unit 20 acquires an image based on a blood flow in the tricuspid valve (hereinafter referred to as a tricuspid regurgitation Doppler image) as a first ultrasonic Doppler image. For example, the Doppler image generating unit 20 acquires an image based on a blood flow in the right ventricular outflow tract (hereinafter referred to as a right ventricular outflow tract Doppler image) as a second ultrasonic Doppler image. The Doppler image generating unit 20 is one example of a first image acquiring unit that acquires a first ultrasonic Doppler image and a second image acquiring unit that acquires a second ultrasonic Doppler image.

The arithmetic operation unit 30, for example, is realized by a processor such as a central processing unit (CPU) executing a program stored in a program memory. In addition, some or all of such functional units may be realized by hardware such as a large scale integration (LSI), an application specific integrated circuit (ASIC), or a field-programmable gate array (FPGA) or may be realized by software and hardware in cooperation.

The arithmetic operation unit 30 derives a reflected component of a pulse pressure wave on the basis of a tricuspid regurgitation Doppler image and a right ventricular outflow tract blood flow Doppler image generated by the Doppler image generating unit 20. The output unit 40 outputs information based on the reflected wave component of the pulse pressure wave derived by the arithmetic operation unit 30. For example, the output unit 40 is a liquid crystal display that displays character information based on the reflected wave component and a result of an arithmetic operation using the reflected wave component.

Figure 2:
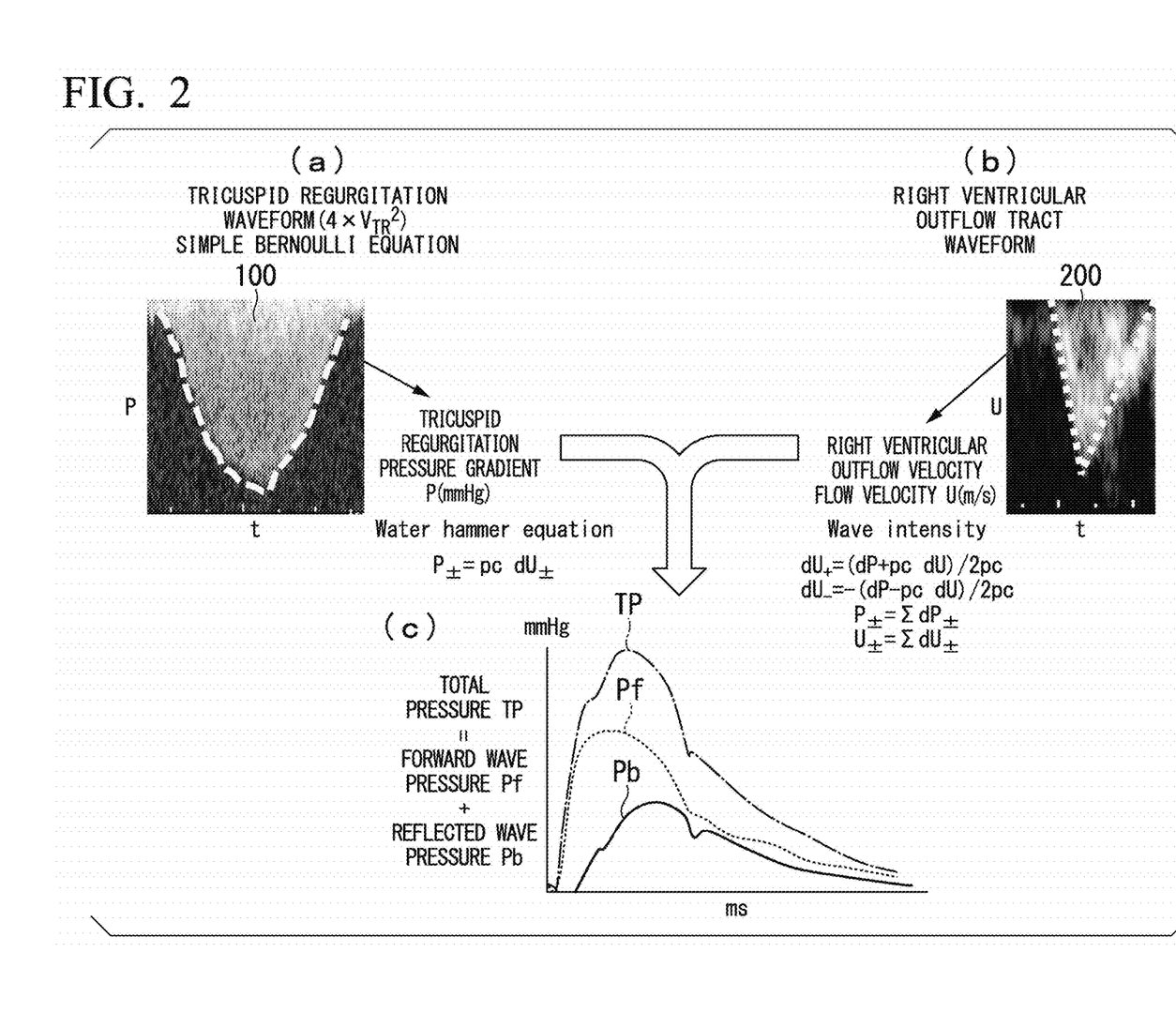
FIG. 2 is a diagram illustrating a reflected wave pressure deriving process in an ultrasonic image processing device according to an embodiment.

FIG. 2 is a diagram illustrating a reflected wave pressure deriving process in an ultrasonic image processing device according to an embodiment.

The arithmetic operation unit 30 acquires a tricuspid regurgitation pressure gradient as illustrated in FIG. 2(a) using a tricuspid regurgitation Doppler image representing a flow velocity of blood that regurgitation flow in a tricuspid valve. By substituting a flow velocity ($V_{TR}$) of a tricuspid regurgitation flow into a simple Bernoulli's equation, the arithmetic operation unit 30 calculates a pressure gradient (P) between a right ventricle and a right atrium in the tricuspid valve. The arithmetic operation unit 30 acquires a pressure gradient P (mmHg) between the right ventricle and the right atrium, which is used for deriving a reflected wave pressure, on the basis of a change (an envelope) in the calculated tricuspid regurgitation velocity.

The arithmetic operation unit 30 acquires a right ventricular outflow tract flow velocity U (m/s), which is used for deriving a reflected wave pressure, from a right ventricular outflow tract blood flow Doppler image as illustrated in FIG. 2(b). In addition, the arithmetic operation unit 30 generates a PU loop (a graph between a pressure and a flow velocity) from a value U acquired from the envelope of the right ventricular outflow tract blood flow Doppler image and determines a slope of the PU loop, thereby estimating a pulse wave speed (c).

The arithmetic operation unit 30 performs arithmetic operations represented by the following Equation 1, Equation 2, and Equation 3 using the pressure difference P (mmHg) between the right ventricle and the right atrium, the right ventricular outflow tract flow velocity U (m/s), the pulse wave speed (c), and a blood density (ρ), thereby calculating a forward wave component (P+) and a reflected wave component (P−) of the pulse pressure wave. In addition, the arithmetic operation unit 30 sets the blood density (ρ) to 1.040.

$$dU+ = (dP + \rho c dU)/2\rho c \qquad \text{(Equation 1)}$$

$$dU- = -(dP - \rho c dU)/2\rho c \qquad \text{(Equation 2)}$$

$$P\pm = \Sigma dP\pm \qquad \text{(Equation 3)}$$

Equation 1, Equation 2, and Equation 3 described above are equations satisfied by the concept of a wave intensity and a water hammer equation. The water hammer equation is represented as below.

$$dP\pm = \rho \cdot c \cdot dU\pm \qquad \text{(Equation 4)}$$

From Equation 4, the pressure gradient P between the right ventricle and the right atrium acquired from the tricuspid valve blood flow Doppler image is substituted into "ρcdU" of Equation 1 and Equation 2, the right ventricular outflow tract flow velocity U, the pulse wave speed (c) and the blood density (ρ) are substituted into Equation 1 and Equation 2, and a forward wave pressure (P+) and a reflected wave pressure (P−) are calculated using Equation 3. By calculating Equation 1, Equation 2, and Equation 3 for every unit time, as illustrated in FIG. 2(c), the arithmetic operation unit 30 acquires a total pressure waveform, a forward wave pressure waveform, and a reflected wave pressure waveform in the pulmonary artery for a measurement period (ms).

Figure 3:
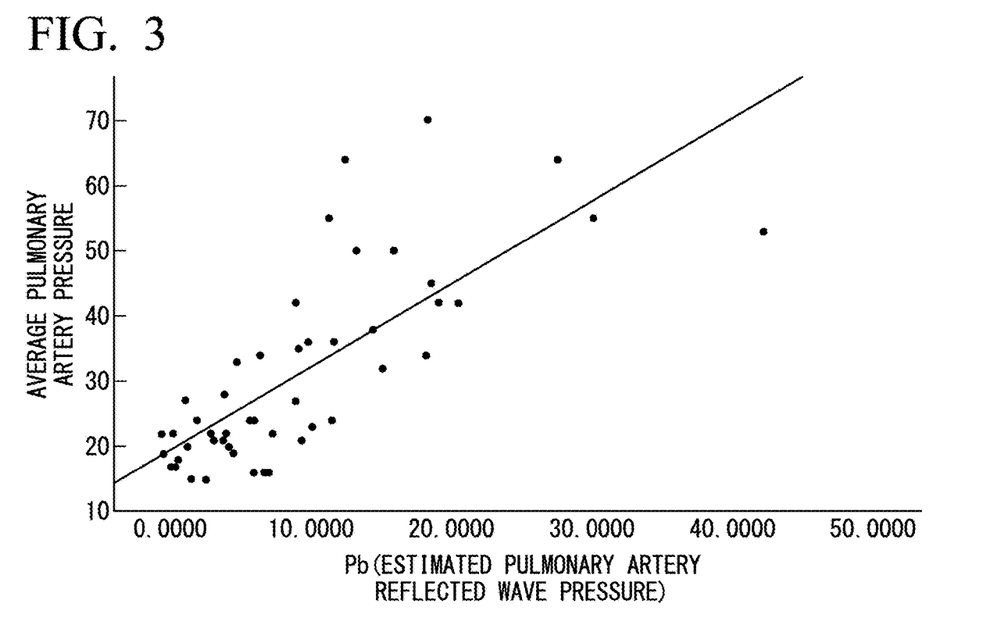
FIG. 3 is a diagram illustrating a correlation between an estimated pulmonary artery reflected wave pressure derived by an ultrasonic image processing device according to an embodiment and an average pulmonary artery pressure.

FIG. 3 is a diagram illustrating a correlation between an estimated pulmonary artery reflected wave pressure derived by an ultrasonic image processing device according to an embodiment and an average pulmonary artery pressure. The average pulmonary artery pressure has an existing value used for a diagnosis of pulmonary hypertension. In addition, the average pulmonary artery pressure has a measurement value acquired by a catheter test. As can be understood from FIG. 3, there is a correlation between the estimated pulmonary artery reflected wave pressure and the average pulmonary artery pressure that is statistically meaningful. In other words, the estimated pulmonary artery reflected wave pressure derived by the ultrasonic image processing device 1 according to the embodiment can be understood as a value representing a pulmonary artery reflected wave pressure and may be regarded as an index that can be used for a clinical diagnosis.

Figure 4:
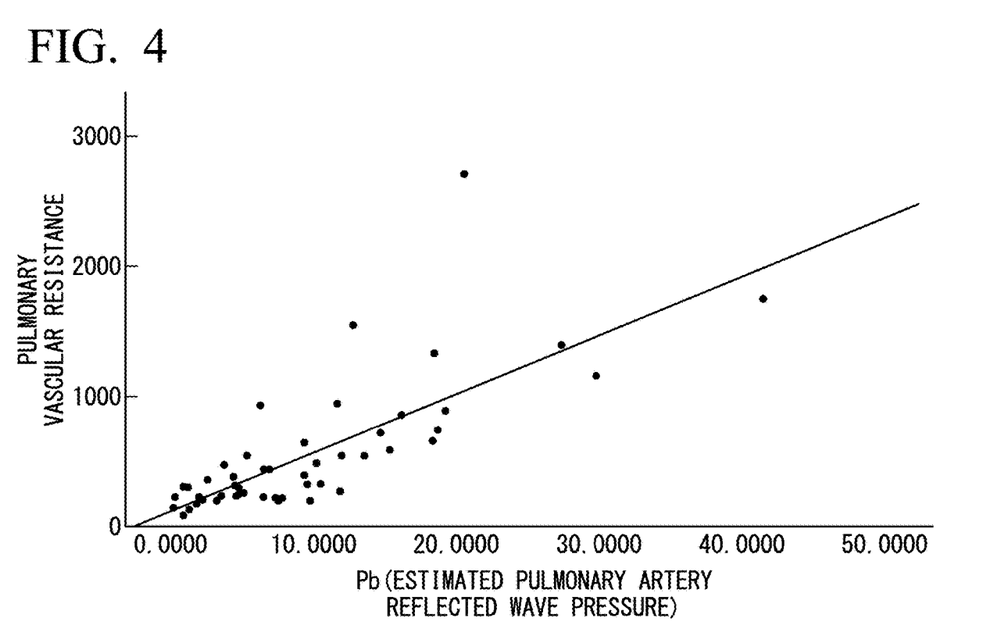
FIG. 4 is a diagram illustrating a correlation between an estimated pulmonary artery reflected wave pressure derived by an ultrasonic image processing device according to an embodiment and pulmonary vascular resistance.

FIG. 4 is a diagram illustrating a correlation between an estimated pulmonary artery reflected wave pressure derived by an ultrasonic image processing device according to an embodiment and pulmonary vascular resistance. As can be understood from FIG. 4, there is a correlation between the estimated pulmonary artery reflected wave pressure derived by the ultrasonic image processing device according to the embodiment and pulmonary vascular resistance. An afterload is pulmonary vascular resistance (PVR) applied when the heart ejects blood. The pulmonary vascular resistance is used not only for a diagnosis of pulmonary hypertension but also for determination of a treatment effect of a pulmonary hypertension disease. Thus, the estimated pulmonary artery reflected wave pressure derived by the ultrasonic image processing device 1 according to the embodiment can be used not only for a diagnosis of pulmonary hypertension but also for determination of a treatment effect of the pulmonary hypertension.

As above, according to the ultrasonic image processing device of the embodiment, it can be understood that an estimated pulmonary artery reflected wave pressure of a high accuracy having a high correlation with an average pulmonary artery pressure and pulmonary vascular resistance can be derived.

Figure 5:
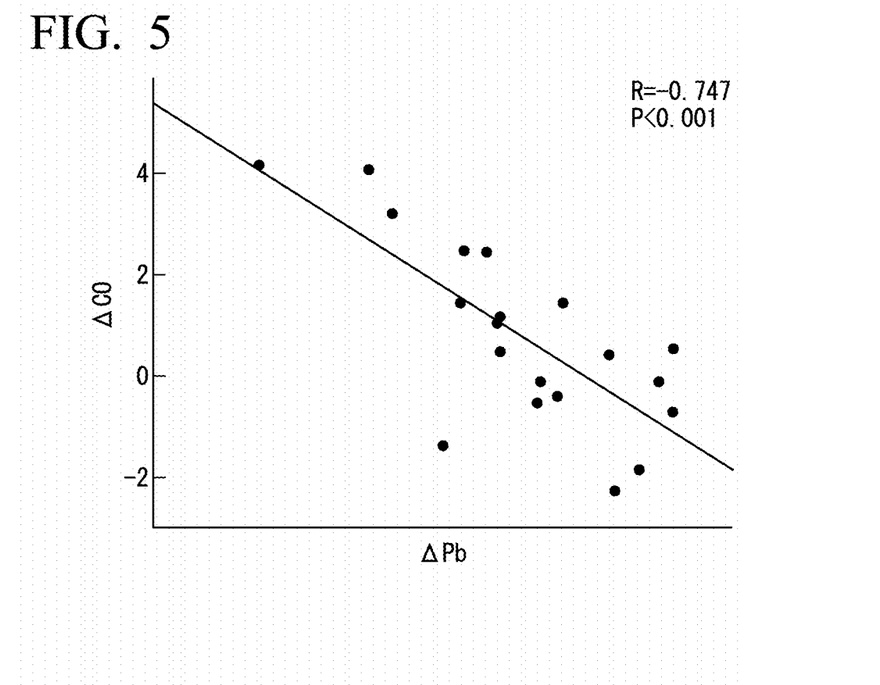
FIG. 5 is a diagram illustrating a correlation between an estimated pulmonary artery reflected wave pressure derived by an ultrasonic image processing device according to an embodiment and a cardiac output change (ΔCardiac Output, ΔCO).
Figure 6:
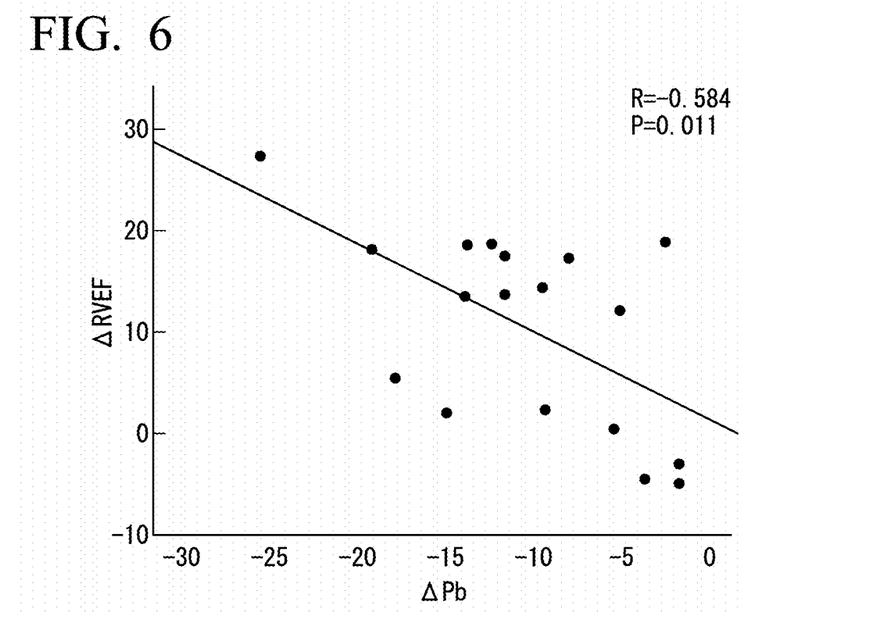
FIG. 6 is a diagram illustrating a correlation between an estimated pulmonary artery reflected wave pressure derived by an ultrasonic image processing device according to an embodiment and a right ventricular ejection fraction change (ΔRight Ventricular Ejection Fraction, ΔRVEF).
Figure 7:
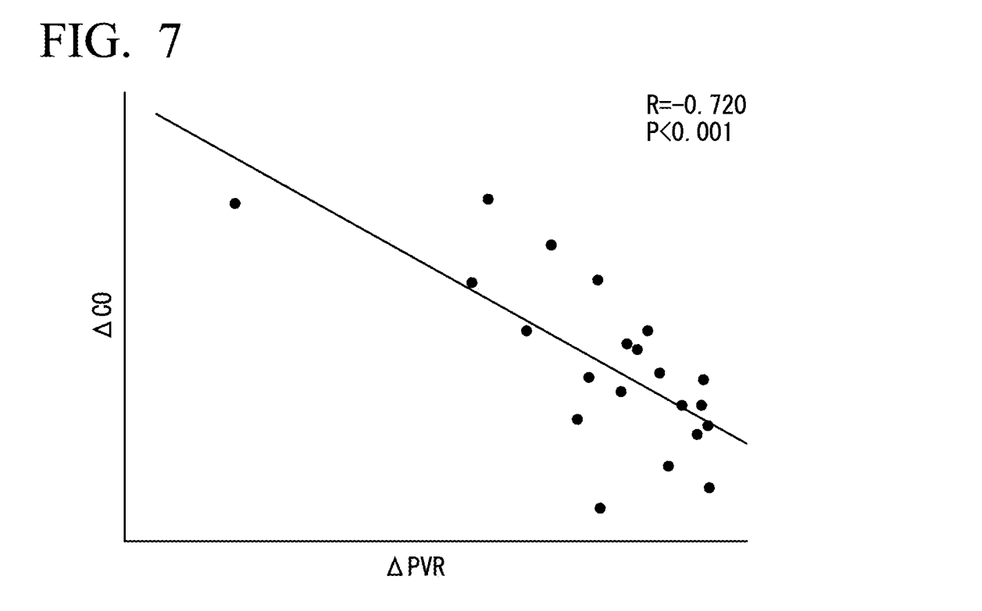
FIG. 7 is a diagram illustrating a correlation between a cardiac output change (ΔCO) and a pulmonary vascular resistance change (ΔPulmonary Vascular Resistance, ΔPVR).
Figure 8:
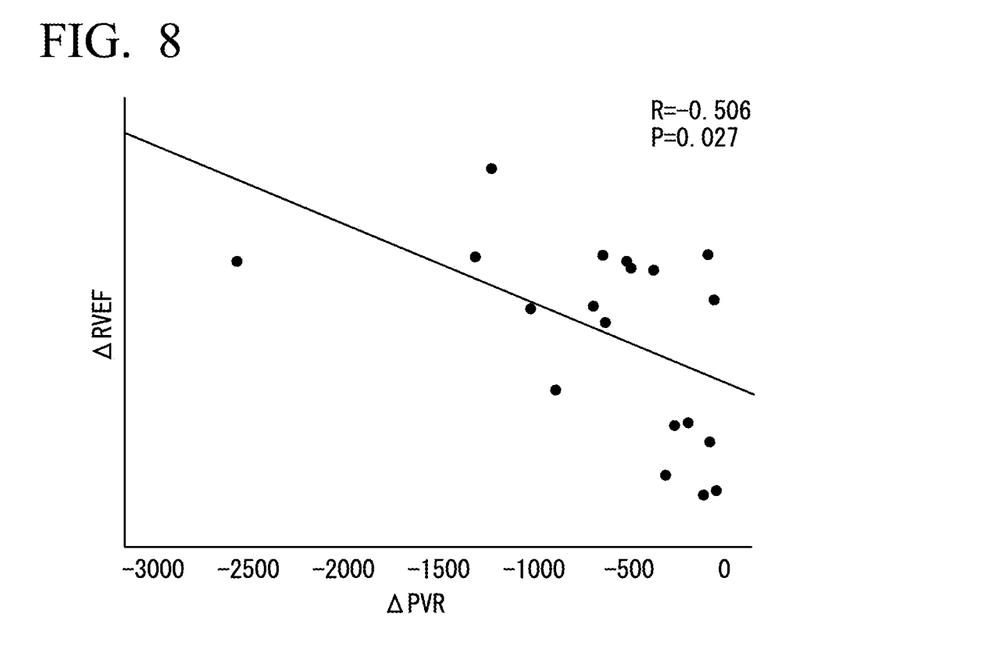
FIG. 8 is a diagram illustrating a correlation between a pulmonary vascular resistance change (ΔPVR) and ΔRVEF.

FIG. 5 is a diagram illustrating a correlation between an estimated pulmonary artery reflected wave pressure derived by an ultrasonic image processing device according to an embodiment and a cardiac output change (ΔCO). FIG. 6 is a diagram illustrating a correlation between an estimated pulmonary artery reflected wave pressure derived by an ultrasonic image processing device according to an embodiment and a right ventricular ejection fraction change (Δ RVEF). FIG. 7 is a diagram illustrating a correlation between a cardiac output change (ΔCO) and a pulmonary vascular resistance change (Δ PVR). FIG. 8 is a diagram illustrating a correlation between a pulmonary vascular resistance change (ΔPVR) and a right ventricular ejection fraction change (ΔRVEF). The cardiac output change (ΔCO), the right ventricular ejection fraction change (ΔRVEF), the estimated pulmonary artery reflected wave pressure (ΔPb), and the pulmonary vascular resistance change (Δ PVR) represented in FIGS. 5 to 8 are differences between measured values before an expansion treatment using a balloon performed in a transcatheter manner and measured values after the treatment for a patient with chronic thromboembolic pulmonary hypertension (CTEPH; a case in which blood clots are stuck in the pulmonary artery).

As can be understood from FIG. 5, there is a correlation between an estimated pulmonary artery reflected wave pressure change (ΔPb) derived by the ultrasonic image processing device according to the embodiment and the cardiac output change (ΔCO). As can be understood from FIG. 6, there is a correlation between the estimated pulmonary artery reflected wave pressure difference (ΔPb) derived by the ultrasonic image processing device according to the embodiment and the right ventricular ejection fraction change (Δ RVEF). As can be understood from FIG. 7, there is a correlation between the pulmonary vascular resistance change (Δ PVR) and the cardiac output change (ΔCO). As can be understood from FIG. 6, there is a correlation between the pulmonary vascular resistance change (ΔPVR) and the right ventricular ejection fraction change (ΔRVEF).

The cardiac output (CO) and the right ventricular ejection fraction (RVEF) are indexes representing movement of the heart. In a case in which the cardiac output (CO) and the right ventricular ejection fraction (RVEF) are low, a prognosis is frequently bad. There are many cases in which the symptom is further enhanced as values of the cardiac output (CO) and the right ventricular ejection fraction (RVEF) become larger. Absolute values of the estimated pulmonary artery reflected wave pressure (Pb) and the pulmonary vascular resistance (PVR) becoming larger represents that the symptom is enhanced by a treatment.

From the results of FIGS. 5 to 8, it can be understood that, although both the estimated pulmonary artery reflected wave pressure change (ΔPb) and the pulmonary vascular resistance change (ΔPVR) have correlations with the cardiac output change (ΔCO) and the correlations right ventricular ejection fraction change (ΔRVEF), the estimated pulmonary artery reflected wave pressure has higher correlations with the cardiac output change (ΔCO) and the right ventricular ejection fraction change (ΔRVEF) than correlations with the pulmonary vascular resistance. In other words, in determination of effects after the treatment, the estimated pulmonary artery reflected wave pressure has a likelihood of being an index superior to the pulmonary vascular resistance. Thus, according to the ultrasonic image processing device 1, by deriving the estimated pulmonary artery reflected wave pressure, an index that is effective for the determination of effects after the treatment can be output.

Figure 9:
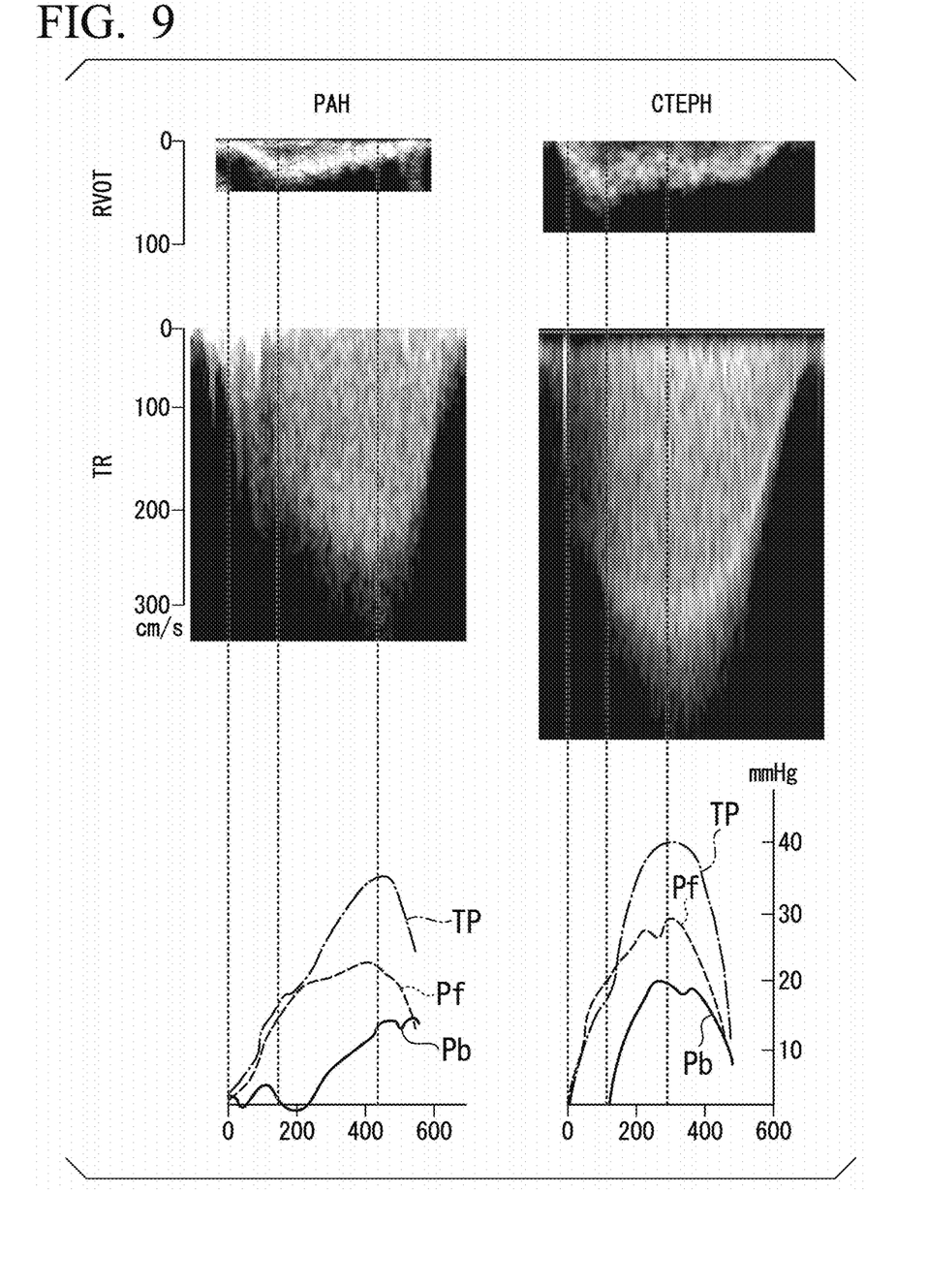
FIG. 9 is a diagram illustrating a relation among a flow velocity and a tricuspid regurgitation pressure gradient in a patient with pulmonary arterial hypertension (PAH), a flow velocity and a tricuspid regurgitation pressure gradient in a patient with chronic thromboembolic pulmonary hypertension (CTEPH), and a total pulmonary artery wave pressure, a forward pressure, and a reflected wave pressure.
Figure 10:
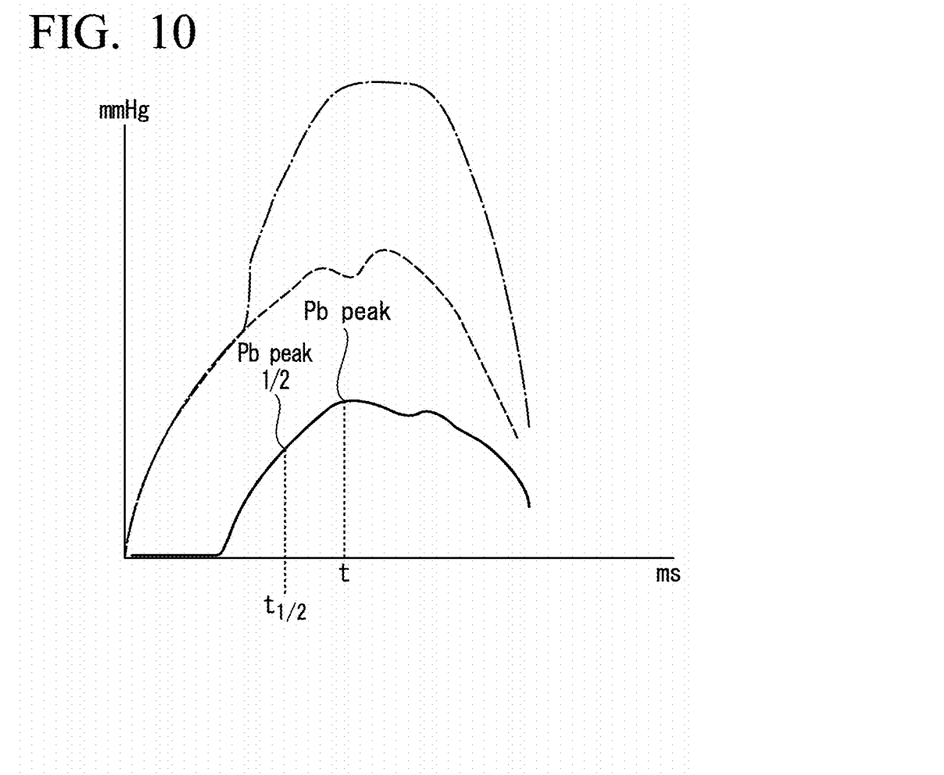
FIG. 10 is a diagram illustrating changes in a total pulmonary artery wave pressure, a forward wave pressure, and a reflected wave pressure over time.

FIG. 9 is a diagram illustrating a relation among a flow velocity and a tricuspid regurgitation Doppler flow in a patient with pulmonary arterial hypertension (PAH), a flow velocity and a tricuspid regurgitation pressure gradient in a patient with chronic thromboembolic pulmonary hypertension (CTEPH), and a total pulmonary artery wave pressure, a forward pressure, and a reflected wave pressure. FIG. 10 is a diagram illustrating changes in a total pulmonary artery wave pressure, a forward wave pressure, and a reflected wave pressure over time.

Figure 11:
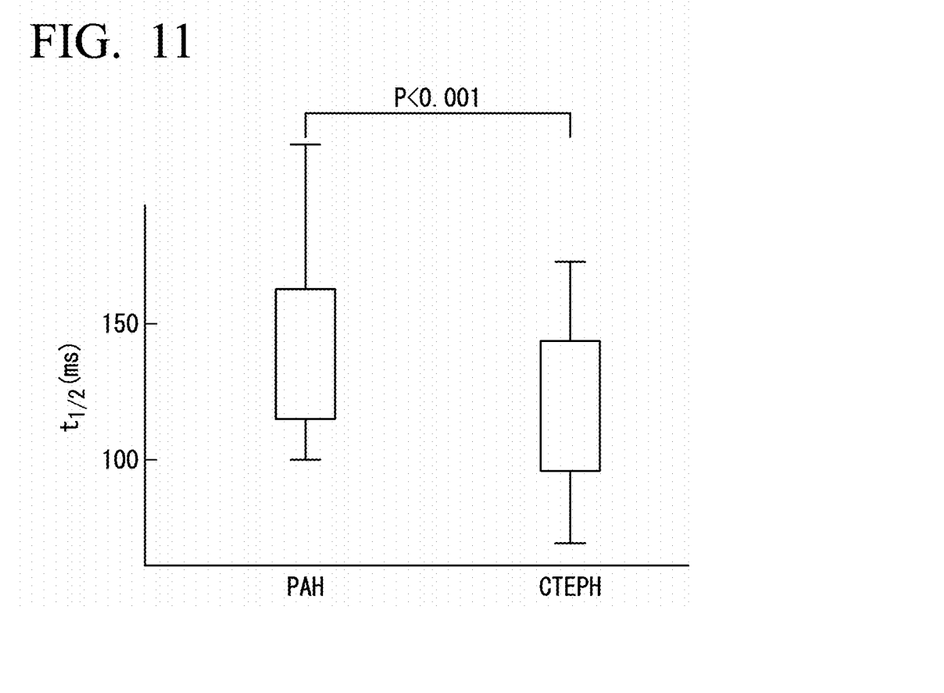
FIG. 11 is a diagram illustrating a half life time ($t_{1/2}$) in a patient with pulmonary arterial hypertension (PAH), a period in a patient with chronic thromboembolic pulmonary hypertension (CTEPH), and a P value.

FIG. 11 is a diagram illustrating a period [ms] in a patent of pulmonary arterial hypertension (PAH), a period [ms] in a patient with chronic thromboembolic pulmonary hypertension (CTEPH), and a P value. As illustrated in FIG. 9, the ultrasonic image processing device 1 acquires a right ventricular outflow tract blood flow Doppler image (RVOT) and a tricuspid regurgitation Doppler flow (TR) image of a patient with pulmonary arterial hypertension (PAH) and derives a total wave pressure (TP), a forward wave pressure (Pf), and a reflected wave pressure (Pb). As illustrated in FIG. 9, the ultrasonic image processing device 1 acquires a right ventricular outflow tract blood flow Doppler image (RVOT) and a tricuspid regurgitation Doppler flow image (TR) of a patient with chronic thromboembolic pulmonary hypertension (CTEPH) and derives a total wave pressure (TP), a forward wave pressure (Pf), and a reflected wave pressure (Pb).

As illustrated in FIG. 10, the ultrasonic image processing device 1 calculates a period between a time (t) at which the reflected wave pressure exhibits a peak value and a time ($t_{1/2}$) at which the reflected wave pressure exhibits a value that is ½ of the peak value for each of a patent of the pulmonary arterial hypertension (PAH) and a patient with the chronic thromboembolic pulmonary hypertension (CTEPH). As illustrated in FIG. 11, it can be understood that the period for the patient with the chronic thromboembolic pulmonary hypertension is meaningfully shorter than the period for the patient with the pulmonary arterial hypertension. This represents that a main place of a lesion of chronic pulmonary thromboembolism is present in a more nerve center portion (thick vasculars) than that of pulmonary artery-related pulmonary hypertension, thus blood ejected from the right ventricular is reflected in a short time, and accordingly, a time until the reflected wave pressure reaches a peak is short. From the result illustrated in FIG. 11, it can be understood that the estimated pulmonary artery reflected wave pressure derived by the ultrasonic image processing device 1 can be used not only for a diagnosis of pulmonary hypertension but also for non-invasively distinguish between the pulmonary artery-related pulmonary hypertension and chronic pulmonary thromboembolism.

For example, according to the ultrasonic image processing device 1 of the embodiment, a period of a time at which the reflected wave pressure reaches a peak value and a time at which the reflected wave pressure reaches ½ of the peak value is compared with a predetermined threshold, and, in a case in which the calculated period is longer than the predetermined threshold, a result indicating that there is a high likelihood of the pulmonary artery-related pulmonary hypertension can be output. In addition, according to the ultrasonic image processing device 1 of the embodiment, a period of a time at which the reflected wave pressure reaches a peak value and a time at which the reflected wave pressure reaches ½ of the peak value is compared with a predetermined threshold, and, in a case in which the calculated period is shorter than the predetermined threshold, a result indicating that there is a high likelihood of the chronic pulmonary thromboembolism can be output. The predetermined threshold is set to a value that can be used for distinguishment between the pulmonary artery hypertension and the chronic thromboembolic pulmonary hypertension using an estimated pulmonary artery reflected wave pressure derived by the ultrasonic image processing device 1.

Figure 12:
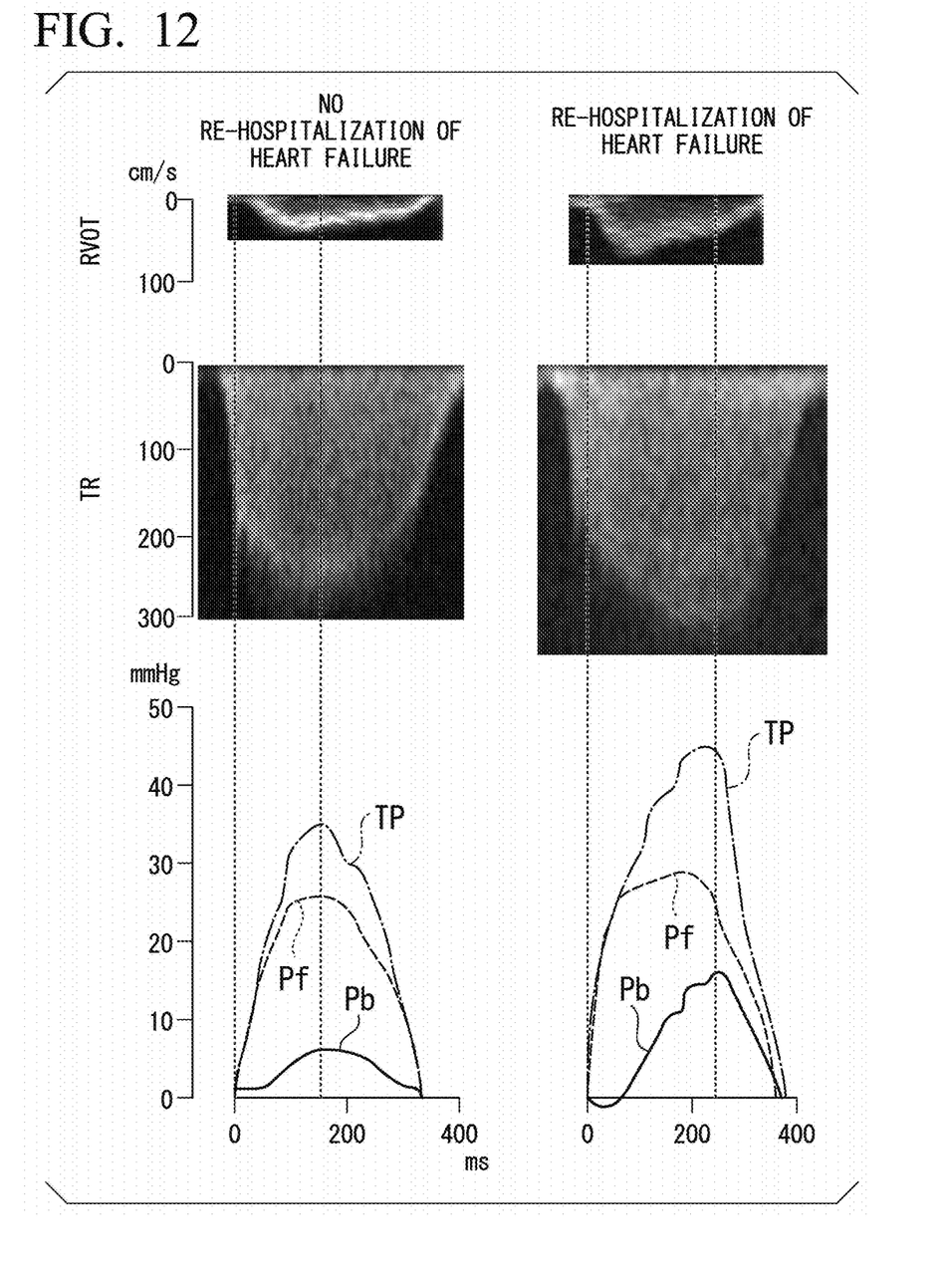
FIG. 12 is a diagram illustrating a relation between a flow velocity and a tricuspid regurgitation pressure gradient in a patient who has not been re-hospitalized and relations of a flow velocity and a tricuspid regurgitation pressure gradient with a total pulmonary artery wave pressure, a forward pressure, and a reflected wave pressure in a patient who has been re-hospitalized.

FIG. 12 is a diagram illustrating a relation between a flow velocity and a tricuspid regurgitation waveform in a patient who has not been re-hospitalized and a relation between a flow velocity and a tricuspid regurgitation waveform and a total pulmonary artery wave pressure, a forward pressure, and a reflected wave pressure in a patient who has been re-hospitalized. As illustrated in the left diagram of FIG. 12, the ultrasonic image processing device 1 acquires a right ventricular outflow tract blood flow Doppler image (RVOT) and a tricuspid regurgitation Doppler flow (TR) for a heart failure patient also having pulmonary hypertension of a symptom stabilization period and derives a total wave pressure (TP), a forward wave pressure (Pf), and a reflected wave pressure (Pb). When a group who has not been re-hospitalized with a heart failure (worsening heart failure, WHF) and a group who has been re-hospitalized are compared with each other, it is understood that a peak of the estimated pulmonary artery reflected wave pressure of a patient who has been re-hospitalized is higher than that of the estimated pulmonary artery reflected wave pressure of a patient who has not been re-hospitalized. Thus, it can be understood that the estimated pulmonary artery reflected wave pressure derived by the ultrasonic image processing device 1 according to the embodiment is an index for predicting prognosis of patients such as a patient who has been re-hospitalized and a patient who has not been re-hospitalized.

Figure 13:
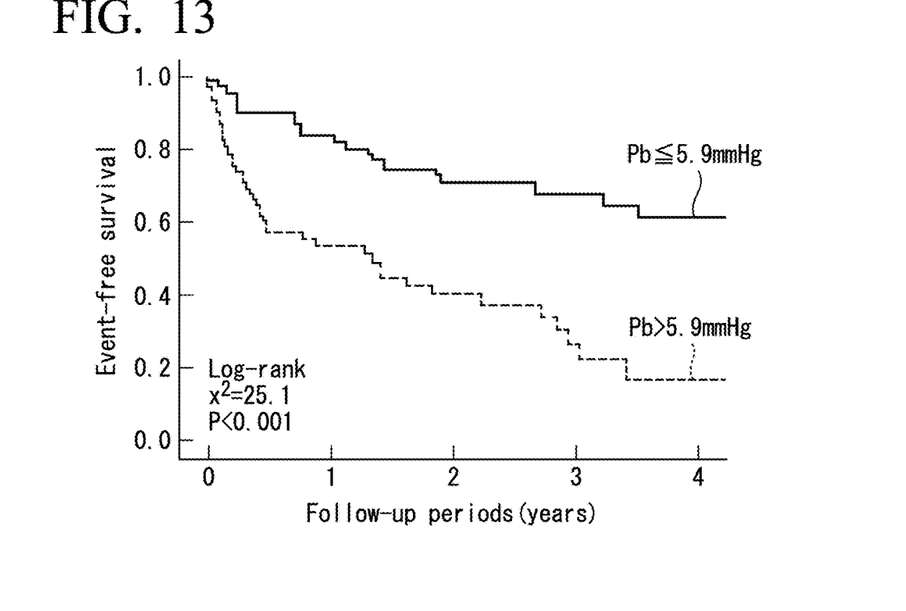
FIG. 13 is an event-free survival (EFS) of a patient whose reflective wave pressure exceeds a predetermined value and event-free survival of a patient whose reflective wave pressure does not exceed the predetermined value.

FIG. 13 is an event-free survival (EFS) of a patient whose reflected wave pressure exceeds a predetermined value and event-free survival of a patient whose reflected wave pressure does not exceed the predetermined value. It can be understood that there is a meaningful difference between event-free survival of a heart-failure patient whose estimated pulmonary artery reflected wave pressure of the heart-failure patient is equal to or lower than a median value and event-free survival of heart-failure patient whose estimated pulmonary artery reflected wave pressure of the heart-failure patient is higher than the median value. In other words, it can be understood that event-free survival of heart-failure patient whose estimated pulmonary artery reflected wave pressure of the heart-failure patient is equal to or lower than a median value is higher than event-free survival of heart-failure patient whose estimated pulmonary artery reflected wave pressure of the heart-failure patient is higher than the median value. For example, the median value of the estimated pulmonary artery reflected wave pressure is 5.9 mmHg Thus, it can be understood that the estimated pulmonary artery reflected wave pressure derived by the ultrasonic image processing device 1 is an index representing event-free survival.

Figure 14:
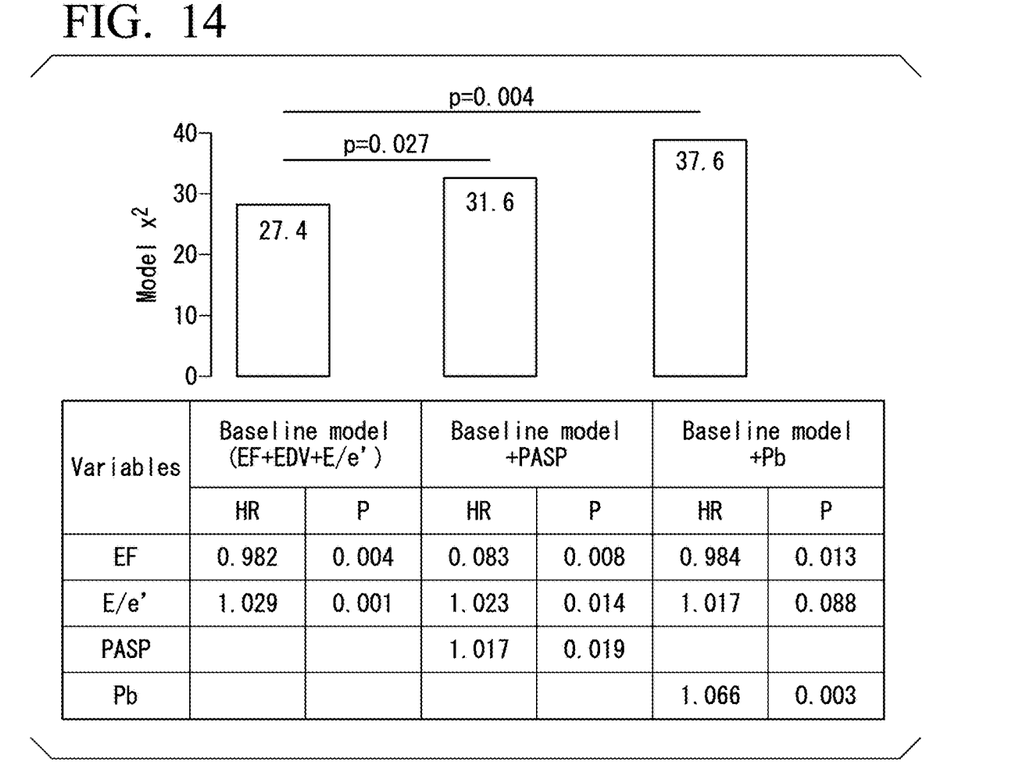
FIG. 14 is a diagram illustrating an existing cardiac function index, a value acquired by adding an estimated pulmonary arterial systolic pressure (PASP) to the existing cardiac function index, and a value acquired by adding an estimated pulmonary artery reflected wave pressure (Pb) to the existing cardiac function index in a comparative manner.

FIG. 14 is a diagram illustrating an existing cardiac function index, a value acquired by adding an estimated pulmonary arterial systolic pressure (PASP) to the existing cardiac function index, and a value acquired by adding an estimated pulmonary artery reflected wave pressure (Pb) to the existing cardiac function index in a comparative manner. The estimated pulmonary arterial systolic pressure (PASP) is an index that is mainly used for a diagnosis of pulmonary hypertension using echocardiography. In FIG. 14, Modelx$^2$ is a statistic, HR is a hazard ratio which is a relative degree of hazard, and p is a P-value of the statistics.

The existing cardiac function index has a value acquired by adding a left ventricular ejection fraction (EF), a left ventricular end-diastolic volume (EDV), and a left ventricular diastolic function (E/e'). When the value acquired by adding the estimated pulmonary arterial systolic pressure (PASP) to the existing cardiac function index and the value acquired by adding the estimated pulmonary artery reflected wave pressure (Pb) to the existing cardiac function index are compared with each other, it is understood that the value acquired by adding the estimated pulmonary artery reflected wave pressure (Pb) to the existing cardiac function index has a stronger relation with prognosis of heart failure re-hospitalization than the value acquired by adding the estimated pulmonary arterial systolic pressure (PASP) to the existing cardiac function index. Thus, according to the ultrasonic image processing device 1 of the embodiment, prognosis of a heart-failure patient also having pulmonary hypertension can be predicted using a reflected wave pressure.

For example, according to the ultrasonic image processing device 1 of the embodiment, by outputting a derived reflected wave pressure with being added to the existing heart function index, information used for predicting prognosis of a heart-failure patient also having pulmonary hypertension can be provided. In addition, although the ultrasonic image processing device 1 according to this embodiment adds the estimated pulmonary artery reflected wave pressure to the existing heart function index, the configuration is not limited thereto, and, by performing an arithmetic operation on the existing heart function index using the estimated pulmonary artery reflected wave pressure, it can be used as an index for a diagnosis or the like.

According to the embodiment described above, an ultrasonic image processing device including: a first image acquiring unit configured to acquire a first ultrasonic Doppler image; a second image acquiring unit configured to acquire a second ultrasonic Doppler image; and an arithmetic operation unit configured to derive a reflected wave component of a pulse pressure wave on the basis of the first ultrasonic Doppler image and the second ultrasonic Doppler image can be realized. According to the ultrasonic image processing device 1 of the embodiment, a reflective wave pressure can be derived non-invasively and with a high accuracy on the basis of two ultrasonic Doppler images.

As described above, an estimated pulmonary artery reflected wave pressure derived by the ultrasonic image processing device 1 has a meaningful correlation with a value of a test using a catheter (FIGS. 3 and 4). As a result, it can be understood that the estimated pulmonary artery reflected wave pressure derived by the ultrasonic image processing device 1 indicates a reflected wave pressure with a high accuracy. In addition, while the diagnostic simulations described above (FIGS. 5 to 8) are performed using an estimated pulmonary artery reflected wave pressure derived by the ultrasonic image processing device 1 according to the embodiment, the estimated pulmonary artery reflected wave pressure derived by the ultrasonic image processing device 1 according to the embodiment has been suggested to be able to be an index having a higher accuracy than the existing established index (the pulmonary vascular resistance (PVR)). As a result, it can be understood that the estimated pulmonary artery reflected wave pressure derived by the ultrasonic image processing device 1 according to the embodiment indicates a reflected wave pressure with a high accuracy.

In addition, according to the ultrasonic image processing device 1 of the embodiment, the invasiveness is low, and thus the process can be performed repeatedly. Furthermore, according to the ultrasonic image processing device 1 of the embodiment, both the first ultrasonic Doppler image and the second ultrasonic Doppler image can be acquired by one ultrasonic Doppler test, and thus a reflected wave pressure of a high accuracy can be acquired without requiring unnecessary efforts of both a doctor and a patient.

According to the ultrasonic image processing device 1 of the embodiment, a reflected wave pressure in the pulmonary artery can be derived with a high accuracy on the basis of an ultrasonic Doppler image based on a blood flow in a tricuspid valve and an ultrasonic Doppler image based on a blood flow in the right ventricular outflow tract.

According to the ultrasonic image processing device 1 according to the embodiment, a pressure value is calculated on the basis of an ultrasonic Doppler image based on a blood flow in a tricuspid valve, a flow velocity value and a pulse wave speed value are calculated on the basis of an ultrasonic Doppler image based on a blood flow in a right ventricular outflow tract, and a forward wave component and a reflected wave component of the pulse pressure wave are calculated on the basis of at least the calculated pressure value, the calculated flow velocity value, the calculated pulse wave speed value, and a blood density. As a result, according to the ultrasonic image processing device 1 of the embodiment, a reflected wave pressure in a pulmonary artery can be derived with a high accuracy.

According to the ultrasonic image processing device 1 of the embodiment, a forward wave component (P+) and a reflected wave component (P−) of the pulse pressure wave can be calculated by performing arithmetic operations represented in the flowing Equation 1, Equation 2, and Equation 3 using the pressure value (P) based on the ultrasonic Doppler image based on the blood flow in the tricuspid valve, the flow velocity value (U) and the pulse wave speed value (c) based on the ultrasonic Doppler image based on the blood flow in the right ventricular outflow tract, and the blood density (ρ) described above.

$$dU+=(dP+\rho cdU)/2\rho c \quad \text{(Equation 1)}$$

$$dU-=-(dP-\rho cdU)/2\rho c \quad \text{(Equation 2)}$$

$$P\pm=\Sigma dP\pm \quad \text{(Equation 3)}$$

According to the ultrasonic image processing device 1 of the embodiment, a value acquired by adding the reflected wave component of the pulse pressure wave to a heart function index is output as a processing result, and thus prediction of prognosis and the like of a heart-failure patient also having pulmonary hypertension with a reflected wave pressure taken into account in existing cardiac function index can be realized.

According to the ultrasonic image processing device 1 of the embodiment, information based on a trend of the reflected wave component of the pulse pressure wave in a time axis is output as a processing result, and thus a diagnosis and the like with the trend of the reflected wave component of the pulse pressure wave with respect to time taken into account can be realized. For example, the ultrasonic image processing device 1 according to the embodiment can perform distinguishment between pulmonary arterial hypertension (PAH) and chronic thromboembolic pulmonary hypertension (CTEPH) non-invasively as described above by outputting a period of a time at which the reflected wave component of the pulse pressure wave becomes a peak value on the time axis and a time at which the reflected wave component of the pulse pressure wave becomes a value that is half the peak value as a processing result.

In addition, according to the embodiment, by using the ultrasonic image processing device 1 described above, an ultrasonic image processing method including: a step of acquiring a first ultrasonic Doppler image; a step of acquiring a second ultrasonic Doppler image; and a step of deriving a reflected wave component of a pulse pressure wave on the basis of the first ultrasonic Doppler image and the second ultrasonic Doppler image can be realized. According to this ultrasonic image processing method, as described above, a reflective wave pressure can be derived non-invasively and with high accuracy on the basis of two ultrasonic Doppler images.

In addition, according to the embodiment, a program causing a computer of the ultrasonic image processing device (diagnosis device) to execute processing of: acquiring a first ultrasonic Doppler image; acquiring a second ultrasonic Doppler image; and deriving a reflected wave component of a pulse pressure wave on the basis of the first ultrasonic Doppler image and the second ultrasonic Doppler image can be realized. According to this program, as described above, a reflective wave pressure can be derived non-invasively and with a high accuracy on the basis of two ultrasonic Doppler images.

In addition, although each embodiment and each modified example have been described, these are examples, thus the disclosed embodiments are not limited thereto, and, for example, any one of each embodiment and each modified example or a part of each embodiment and a part of each modified example may be combined with other one or a plurality of embodiments or other one or a plurality of modified examples for realizing one aspect of the disclosed embodiments.

In addition, by recording a program for performing each process of the ultrasonic image processing device 1 according to this embodiment in a computer-readable recording medium and causing a computer system to read and execute the program recorded in this recording medium, various processes relating to the ultrasonic image processing device 1 described above may be performed.

The "computer system" described here includes an operating system (OS) and hardware such as peripherals. In addition, in a case in which a WWW system is used, "computer system" also includes a home page providing environment (or a display environment). Furthermore, the "computer-readable recording medium" represents a writable nonvolatile memory such as a flexible disk, a magneto-optical disk, a ROM, or a flash memory, a portable medium such as a CD-ROM, or a storage device such as a hard disk built into the computer system.

In addition, the "computer-readable recording medium" includes a medium storing the program for a predetermined time such as internal volatile memory (for example, a Dynamic Random Access Memory (DRAM)) of a computer system serving as a server or a client in a case in which the program is transmitted through a network such as the Internet or a communication line such as a telephone line. In addition, the program described above may be transmitted from a computer system storing this program in a storage device or the like to another computer system through a transmission medium or a transmission wave in a transmission medium.

Here, the "transmission medium" transmitting a program represents a medium having an information transmitting function such as a network (communication network) including the Internet and the like or a communication line (communication wire) including a telephone line. The program described above may be used for realizing a part of the functions described above. In addition, the program described above may be a program realizing the functions described above by being combined with a program recorded in the computer system in advance, a so-called a differential file (differential program).

As above, although the embodiment has been described in detail with reference to the drawings, a specific configuration is not limited to this embodiment, and a design and the like in a range not departing from the concept of the disclosed embodiments are included therein.

According to an ultrasonic image processing device of this embodiment, a reflective wave pressure of blood can be derived non-invasively and with a high accuracy.

What is claimed is:
1. An ultrasonic image processing device comprising:
 a first image acquiring device configured to acquire a first ultrasonic Doppler image, wherein the first ultrasonic Doppler image is an image based on a blood flow in a tricuspid valve;

a second image acquiring device configured to acquire a second ultrasonic Doppler image, wherein the second ultrasonic Doppler image is an image based on a blood flow in a right ventricular outflow tract; and an arithmetic operator configured to derive a reflected wave component of a pulse pressure wave on a basis of the first ultrasonic Doppler image and the second ultrasonic Doppler image, wherein the arithmetic operator operates to, calculate a pressure value on the basis of the first ultrasonic Doppler image;

calculate a flow speed value and a pulse wave speed value on the basis of the second ultrasonic Doppler image; and calculate an advancing wave component and a reflected wave component of the pulse pressure wave on the basis of at least the calculated pressure value, the calculated flow speed value, the calculated pulse wave speed value, and a blood density.

2. The ultrasonic image processing device according to claim 1,
wherein the arithmetic operator calculates the forward wave component (P+) and the reflected wave component (P−) of the pulse pressure wave by performing arithmetic operations represented in the following Equation 1, Equation 2, and Equation 3 using the pressure value (P) based on the first ultrasonic wave Doppler image, the flow velocity value (U) and the pulse wave speed value (c) based on the second ultrasonic Doppler image, and the blood density (p);

$$dU+ = (dP + pcdU)/2pc \quad \text{(Equation 1)}$$

$$dU- = -(dP - pcdU)/2pc \quad \text{(Equation 2)}$$

$$P\pm = \Sigma dP\pm \quad \text{(Equation 3)}$$

3. The ultrasonic image processing device according to claim 1, wherein the arithmetic operator outputs a value acquired by adding the reflected wave component of the pulse pressure wave to a heart function index as a processing result.

4. The ultrasonic image processing device according to claim 1, wherein the arithmetic operator outputs information based on a trend of the reflected wave component of the pulse pressure wave on a time axis as a processing result.

5. The ultrasonic image processing device according to claim 4, wherein the arithmetic operator outputs a period of a time at which the reflected wave component of the pulse pressure wave becomes a peak value on the time axis and a time at which the reflected wave component of the pulse pressure wave becomes a value that is half the peak value as a processing result.

6. An ultrasonic image processing method comprising:
acquiring a first ultrasonic Doppler image, the first ultrasonic Doppler image being an image based on a blood flow in a tricuspid valve;
acquiring a second ultrasonic Doppler image, the second ultrasonic Doppler image being an image based on a blood flow in a right ventricular outflow tract; and
deriving a reflected wave component of a pulse pressure wave on a basis of the first ultrasonic Doppler image and the second ultrasonic Doppler image, wherein the deriving includes,
calculating a pressure value on the basis of the first ultrasonic Doppler image;
calculating a flow speed value and a pulse wave speed value on the basis of the second ultrasonic Doppler image; and
calculating an advancing wave component and a reflected wave component of the pulse pressure wave on the basis of at least the calculated pressure value, the calculated flow speed value, the calculated pulse wave speed value, and a blood density.

7. A non-transitory computer readable medium causing a computer of a diagnosis device to execute processing of:
acquiring a first ultrasonic Doppler image, wherein the first ultrasonic Doppler image is an image based on a blood flow in a tricuspid valve;
acquiring a second ultrasonic Doppler image, wherein the second ultrasonic Doppler image is an image based on a blood flow in a right ventricular outflow tract; and
deriving a reflected wave component of a pulse pressure wave on a basis of the first ultrasonic Doppler image and the second ultrasonic Doppler image, wherein the deriving includes:
calculating a pressure value on the basis of the first ultrasonic Doppler image;
calculating a flow speed value and a pulse wave speed value on the basis of the second ultrasonic Doppler image; and
calculating an advancing wave component and a reflected wave component of the pulse pressure wave on the basis of at least the calculated pressure value, the calculated flow speed value, the calculated pulse wave speed value, and a blood density.

* * * * *